US00PP28959P2

(12) United States Plant Patent
Yanny

(10) Patent No.: US PP28,959 P2
(45) Date of Patent: Feb. 13, 2018

(54) ***SYRINGA* PLANT NAMED 'JN UPRIGHT SELECT'**

(50) Latin Name: *Syringa patula*
Varietal Denomination: JN Upright Select

(71) Applicant: JN Plant Selections, LLC, Milwaukee, WI (US)

(72) Inventor: Michael D. Yanny, Milwaukee, WI (US)

(73) Assignee: JN PLANT SELECTIONS, LLC, Milwaukee, WI (US)

( * ) Notice: Subject to any disclaimer, the term of this patent is extended or adjusted under 35 U.S.C. 154(b) by 0 days.

(21) Appl. No.: 15/330,648

(22) Filed: Oct. 24, 2016

(51) Int. Cl.
*A01H 5/00* (2006.01)

(52) U.S. Cl.
USPC ..... Plt./248

(58) Field of Classification Search
USPC ..... Plt./248
See application file for complete search history.

*Primary Examiner* — Annette H Para
(74) *Attorney, Agent, or Firm* — Penny J. Aguirre

(57) ABSTRACT

A new cultivar of *Syringa patula* plant named 'JN Upright Select' that is characterized by its upright plant habit, its large, fragrant inflorescences that are light violet in color, its good rooting habit as it readily roots from softwood stem cuttings, its good cold hardiness with hardiness at least to U.S.D.A. 3b even as young plants, its fall foliage that is reddish purple and yellow in center in most seasons in southern Wisconsin, and its good production characteristics, and its moderate resistance to root rot and good resistance to powdery mildew.

2 Drawing Sheets

Botanical classification: *Syringa patula.*
Variety denomination: 'JN Upright Select'.

CROSS REFERENCE TO A RELATED APPLICATION

This application is co-pending with a U.S. Plant Patent Application filed for a plant derived from the same breeding program that is entitled *Syringa* Plant Named 'Pink Flower Select' (U.S. Plant patent application Ser. No. 15/530,155).

BACKGROUND OF THE INVENTION

The present invention relates to a new and distinct cultivar of *Syringa patula* and will be referred to hereafter by its cultivar name, 'JN Upright Select'. 'JN Upright Select' is a new cultivar of lilac grown for use as an ornamental landscape with particular use as a hedging plant.

The new cultivar of *Syringa* arose from a breeding program conducted by the Inventor in Menomonee Falls, Wis. 'JN Upright Select' originated as a seedling that arose from seed planted from the open pollination of *Syringa patula* 'Miss Kim' (not patented) in the autumn of 1990. 'JN Upright Select' was selected as a single unique plant in June of 2005 from amongst the resulting seedlings.

Asexual propagation of the new cultivar was first accomplished by the Inventor by softwood stem cuttings in the summer of 2005 in Menomonee Falls, Wis. Asexual propagation of the new cultivar by softwood stem cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'JN Upright Select' as a unique cultivar of *Syringa.*

1. 'JN Upright Select' exhibits a an upright plant habit.
2. 'JN Upright Select' exhibits large, fragrant inflorescences that are light violet in color.
3. 'JN Upright Select' exhibits a good rooting habit as it readily roots from softwood stem cuttings.
4. 'JN Upright Select' exhibits good cold hardiness with hardiness at least to U.S.D.A. 3b, even as young plants.
5. 'JN Upright Select' exhibits fall foliage that is reddish purple and yellow in center in most seasons in souther Wisconsin.
6. 'JN Upright Select' exhibits some resistance to root rot and good resistance to powdery mildew.

The female parent of 'JN Upright Select', 'Miss Kim', differs from 'JN Upright Select' in having smaller inflorescences and in being shorter in height with a less upright plant habit. The new *Sryinga* can also be compared to the *Syringa* cultivars 'KLMone' (not patented) and 'Pink Flower Select'. 'KLMone' differs from 'JN Upright Select' in having a less upright plant habit, and in having flowers that are light pink in color. 'Pink Flower Select' is similar to 'JN Upright Select' in having a floriferous bloom habit, in having large inflorescences, and in having resistance to root rot and powdery mildew. 'Pink Flower Select' differs from 'JN Upright Select' in having flowers that are light pink in color and in having a less upright plant habit.

BRIEF DESCRIPTION OF THE DRAWINGS

The accompanying colored photographs illustrate the overall appearance and distinct characteristics of the new *Syringa*. The photographs in FIG. 1 and FIG. 4 were taken of a 9 year-old plant and the photographs in FIG. 1 and FIG. 2 was taken of a 7 year-old plant as grown outdoors in a nursery in Menomonee, Wis.

The photograph in FIG. 1 provides a side view of a plant of 'JN Upright Select' in bloom.

Figure 1:
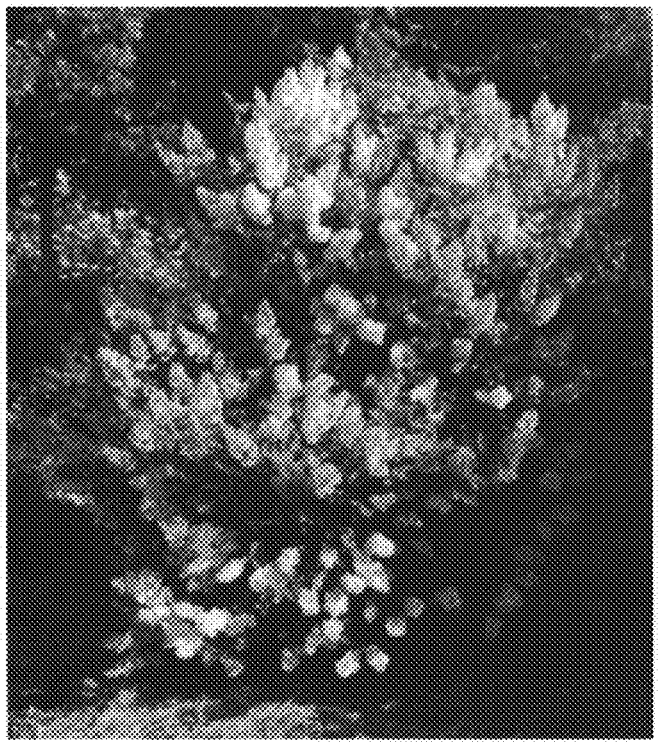
Figure 2:
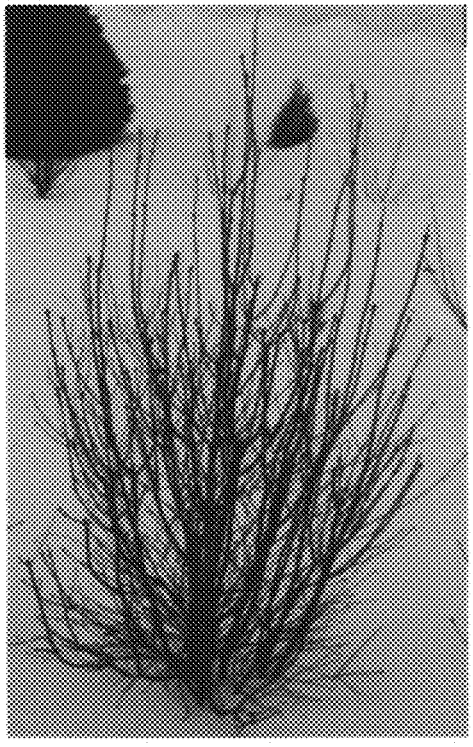

The photograph in FIG. 2 provides a view of the upright branching of 'JN Upright Select'.

The photograph in FIG. 2 provides a view of the inflorescences of 'JN Upright Select'.

Figure 3:
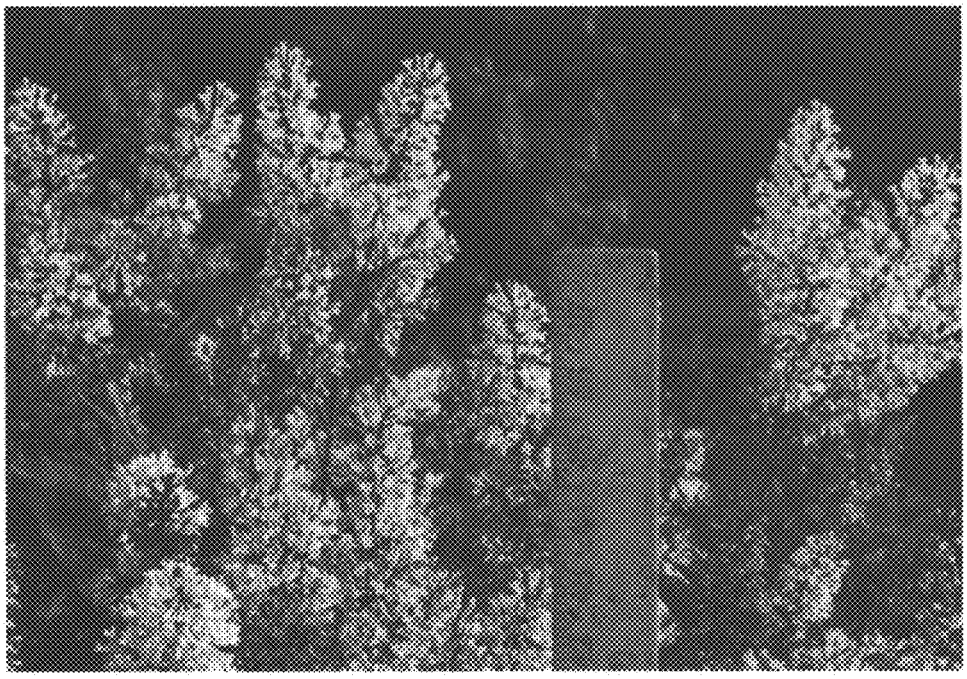
Figure 4:
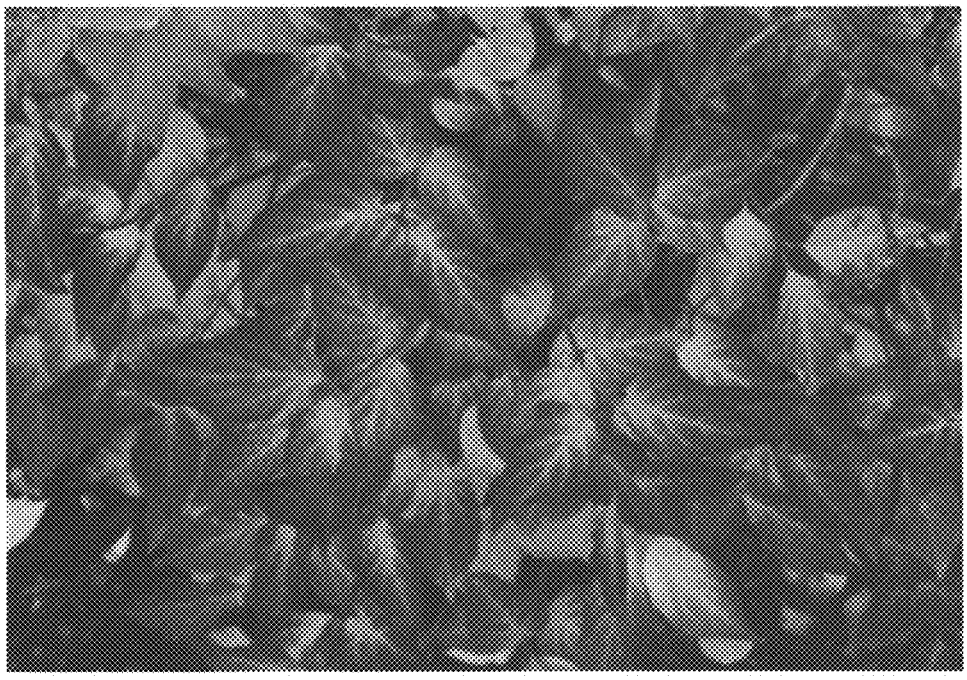

The photograph in FIG. 3 provides a close-up view of the disease-free fall foliage of 'JN Upright Select'.

The colors in the photographs are as close as possible with the photographic and printing technology utilized and the color values cited in the detailed botanical description accurately describe the colors of the new *Syringa*.

DETAILED BOTANICAL DESCRIPTION

The following is a description of 2 year-old plants as grown outdoors in a two gallon container and 7 to 9 year-old plants as grown outdoors in a trial plot in Menomonee Falls, Wis. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Two to three weeks in mid to late spring, warm temperatures shorted blooming period.

*Plant habit*.—Upright and densely branched (becomes slightly less upright as a mature plant).

*Height and spread*.—An average of 1.8 m in height and 1.5 m in spread for 9 year old plants in the landscape.

*Hardiness*.—At least hardy in U.S.D.A. Zone 3b to 7.

*Diseases and pests*.—Some resistance to root rot (*Phytophthora* spp) and good resistance to powdery mildew (*Microsphaera penicullata*) has been observed.

*Root description*.—Fibrous, blend of 158A and 161A in color.

*Propagation*.—Softwood stem cuttings.

*Root development*.—Softwood cuttings root readily in 6 to 8 weeks in a hot house under intermittent mist, rooted cuttings are easily overwintered and roots will fully develop in a one-quart container by mid-summer the following year.

*Growth rate*.—Moderate, two flushes of growth pers season in Wisconsin.

Stem description:

*Shape*.—Rounded.

*Stem color*.—One year-old wood; 3 year-old wood; a blend of 198A and 198B.

*Stem size*.—One year lateral branch; 17 to 30 cm in length and 3 to 4 mm in width.

*Stem surface*.—Surface is glabrous, dull and slightly bark-like with lenticels; an average of 26 lenticels per 1 cm in length, 159A in color, average of 1 mm in diameter.

*Internode length*.—1 to 2 cm on on non-vigorous branches and 5.5 to 7 cm on vigrous branches.

*Branching*.—Branches held at an angle of 30° to main branch.

Foliage description: ($1^{st}$ flush (early spring growth) and $2^{nd}$ flush of foliage (late spring) with.

*Two flushes of foliage*.—$1^{st}$ flush (early spring) and $2^{nd}$ flush of foliage (late spring) with differences noted.

*Leaf shape*.—$1^{st}$ flush; ovate to broadly ovate, $2^{nd}$ flush; ovate to lanceolate.

*Leaf division*.—Simple.

*Leaf base*.—Cuneate.

*Leaf apex*.—Acuminate.

*Leaf fragrance*.—None.

*Leaf venation*.—Pinnate, upper surface color; closest to N144A and slighty transluscent on young leaves, lower surface color matches leaf color and slighty transluscent on young leaves; color changes to 150B in the fall.

*Leaflet margins*.—$1^{st}$ flush; entire and slightly undulate, $2^{nd}$ flush; entire with pronounced undulations.

*Leaf arrangement*.—Opposite to pseudoverticillate.

*Leaf attachment*.—Petiolate.

*Leaf surface*.—Both surfaces are dull, lower surface is sparsely covered with tiny puberlent hairs that match the leaf color and <1 mm in length.

*Leaf size*.—$1^{st}$ flush; 7.3 to 8.5 cm in length and 4.5 to 5.4 cm in width, $2^{nd}$ flush; 4.3 o 5.3 cm in length and 1.7 to 2.4 cm in width.

*Leaf quantity*.—An average of 126 leaves per branch 15 cm in length.

*Leaf color*.—$1^{st}$ flush; 147B on upper surface and 147C on lower surface, $2^{nd}$ flush; 147A on upper surface and 147B on lower surface, fall; 187A with center and veins 150B with less sun exposure (north side of plant) promarily 7C and tinged with 187A.

*Petioles*.—$1^{st}$ flush; 1.1 to 1.3 cm in length and 1 mm in width, $2^{nd}$ flush; 5 to 7 mm in length, color matches leaf coloration, surface glabrous.

*Bracts*.—An average of 2, occasionally 4 at the base of a leaf cluster when emerging, 5 mm in length and 4 mm in width, upper and lower surfaces dull and glabrous, 144C in color.

Inflorescence description:

*Inflorescence type*.—Thyrse compound panicles on terminals and laterals of previous years' growth, ovate in overall shape.

*Inflorescence size*.—An average of 30 cm in length and 15 cm in width.

*Rachis*.—Rounded in shape, an average of 14 cm in length and 2.5 mm in diameter, 147B in color with lenticels 0.5 mm in length and 165D in color, surface is glabrous, strong strength.

*Peduncles*.—An average of 4 cm in length and 1 mm in width, 147B in color, glabrous surface, medium strong strength.

*Flower buds*.—Spatulate in shape, an average of 9 mm in depth and 3 mm diameter at the apex tapering to 1.5 mm at the base, color; 84A to 84B at apex transitioning to a 84D and 85D near the base.

*Flower fragrance*.—Sweet lilac scent.

*Persistence of flowers*.—Self-cleaning, calyx persistent.

*Lastingness of flowers*.—Individual panicles bloom for about 2 weeks, depending on temperature.

*Flower quantity*.—An average of 212 flowers per compound panicle.

*Flower type*.—Salverform with spreading petals.

*Flower aspect*.—Upwards and outward.

*Flower size*.—An average of 6.5 mm in diameter and 11.5 mm in depth.

*Petals*.—4, an average of 3 mm in length and 1.5 mm in width, lower 80% fused forming a narrow tube, entire margin, acute apex, free portion ovate in shape, upper and lower surfaces smooth and glabrous, color; upper and lower surfaces a 76C to 76D.

*Calyx.*—Campanulate, an average of 1.5 mm in depth and 1 mm in width, comprised of 4 fused sepals with free acute apices, glabrous surface, 139C in color.

Reproductive organs:

*Pistils.*—1, inserted deep into calyx, an average of 3 mm in length, stigma; minute in size, oval in shape, 150D in color, style; 155A in color.

*Stamens.*—2, extend beyond corolla, anthers; an average of 1.5 mm in length and 182C in color filaments; about 5.5 mm in length, pollen; abundant in quantity and 1A in color.

*Fruit and seed.*—Seed capsules; an average of 1.4 cm in length and 2.5 mm in width, 146C in color darkening to 200D, covered with about 50 lenticels 155D in color and 0.5 mm in length, seed; (if present) an average of 1.15 cm in length and 2 mm in width, 175A in color.

It is claimed:

1. A new and distinct cultivar of *Syringa* plant named 'JN Upright Select' as herein illustrated and described.

* * * * *